United States Patent
Lefebvre et al.

(10) Patent No.: US 9,351,474 B2
(45) Date of Patent: May 31, 2016

(54) DISINFESTATION PROCESS

(75) Inventors: Philippe Lefebvre, Cottenchy (FR);
Magali Riglet, Viroflay (FR)

(73) Assignee: SOLVAY SA, Brussels (BE)

( * ) Notice: Subject to any disclaimer, the term of this patent is extended or adjusted under 35 U.S.C. 154(b) by 86 days.

(21) Appl. No.: 14/115,898

(22) PCT Filed: May 14, 2012

(86) PCT No.: PCT/EP2012/058949
§ 371 (c)(1),
(2), (4) Date: Nov. 6, 2013

(87) PCT Pub. No.: WO2012/152952
PCT Pub. Date: Nov. 15, 2012

(65) Prior Publication Data
US 2014/0069348 A1    Mar. 13, 2014

(30) Foreign Application Priority Data

May 12, 2011 (FR) ..................... 11 54102
May 31, 2011 (FR) ..................... 11 54773

(51) Int. Cl.
| | | |
|---|---|---|
| A01K 27/00 | (2006.01) |
| A01K 1/00 | (2006.01) |
| A01M 1/20 | (2006.01) |
| A01N 59/00 | (2006.01) |
| A01K 13/00 | (2006.01) |
| A01N 55/02 | (2006.01) |

(52) U.S. Cl.
CPC . A01K 1/00 (2013.01); A01K 13/00 (2013.01); A01M 1/2027 (2013.01); A01N 55/02 (2013.01); A01N 59/00 (2013.01)

(58) Field of Classification Search
CPC ........................... A01K 1/0047; A01K 27/003
USPC ........................................... 119/795
See application file for complete search history.

(56) References Cited

U.S. PATENT DOCUMENTS

| | | | |
|---|---|---|---|
| 2,860,453 A | 11/1958 | Frey | |
| 3,364,900 A | 1/1968 | Knapp | |
| 6,029,608 A | 2/2000 | Johnson | |
| 6,312,507 B1* | 11/2001 | Taylor et al. | 96/19 |
| 8,663,551 B1* | 3/2014 | Moore, Jr. | 422/4 |
| 2002/0076348 A1* | 6/2002 | Schneider et al. | 422/5 |
| 2011/0061601 A1* | 3/2011 | Correa et al. | 119/437 |
| 2011/0146582 A1* | 6/2011 | Lemmon et al. | 119/448 |
| 2013/0087103 A1* | 4/2013 | Glazman | 119/448 |

FOREIGN PATENT DOCUMENTS

| | | |
|---|---|---|
| EP | 2098116 A1 | 9/2009 |
| FR | 1161937 A | 9/1958 |
| FR | 2915902 A1 | 11/2008 |
| WO | WO 0135744 A1 | 5/2001 |
| WO | WO 02102158 A1 | 12/2002 |
| WO | WO 2004032626 A2 | 4/2004 |
| WO | WO 2005025317 A1 | 3/2005 |
| WO | WO 2006097480 A1 | 9/2006 |
| WO | WO 2006097504 A2 | 9/2006 |
| WO | WO 2009002465 A2 | 12/2008 |

OTHER PUBLICATIONS

U.S. Appl. No. 11/908,863, Jean-Philippe Pascal, et al, filed Sep. 4, 2007.

* cited by examiner

*Primary Examiner* — Kristen C Hayes
(74) *Attorney, Agent, or Firm* — Beatrice C. Ortego

(57) ABSTRACT

Process for controlling the development of parasites in an animal environment equipped with an air introduction device, according to which a parasiticidal powder composition is introduced into the air introduction device, preferably according to which the air introduction device comprises one or more point(s) of introduction of air into the animal environment located close to the animal droppings. The invention also relates to the use of the process, to the use of a parasiticidal composition in an air introduction device for controlling the development of parasites in an animal environment, to a device for controlling the development of parasites in the animal environment, and to a livestock building equipped with such a device.

21 Claims, No Drawings

DISINFESTATION PROCESS

CROSS-REFERENCE TO RELATED APPLICATIONS

The present application is a U.S. national stage entry under 35 U.S.C. §371 of International Application No. PCT/EP2012/058949 filed May 14, 2012, which claims priority benefit to French patent applications FR 11.54102, filed on May 12, 2011 and FR 11.54773, filed on May 31, 2011, the whole content of each of these patent applications being herein incorporated by reference for all purposes.

TECHNICAL FIELD

The invention relates to a disinfestation process. The invention relates more particularly to a process for disinfesting the environment of animals by introducing a parasiticidal powder composition into the aeration device of the said environment. The invention also relates to a device for controlling the development of parasites in the environment of animals, and to a livestock building equipped with such a device.

The term parasiticidal composition means a composition on contact with which the parasites that tend to develop especially on livestock animals, pets or man cannot survive.

The term "parasites" means arthropods such as insects, mites, fleas, flies and ticks.

The parasites may be in the egg, larval or adult stage. The action of the composition may be direct. It may also be indirect, for example when the parasiticidal composition destroys a substance necessary to the survival of the parasite.

TECHNICAL BACKGROUND

The development of parasites on livestock and pets is a well-known worrying problem. It may have major consequences on hygiene and the propagation of certain diseases in the case of livestock rearing, such as: salmonellosis especially in aviculture, enterocolitis, verminosis, mastitis and keratoconjunctivitis in cattle, foot-and-mouth disease, swine fever, erysipelothrix infection and myxomatosis in rabbits. This development may have major consequences on the economic productivity of the livestock business, especially in aviculture, and in particular on the rearing of table chickens, and turkeys, and laying hens.

It is especially known practice to combat parasites using neurotoxic substances and growth inhibitors such as synthetic pyrethroids, organophosphorus compounds or carbamates, for example. These products are applied either by spraying or by thermo-nebulization. Their uses are, for the vast majority of the products, prohibited in the presence of animals. The reason for this is that these substances have the drawback of also being toxic to the animal on which the parasites develop. Some of these substances also have an allergenic nature to man or animals. When the rearing of the animal is intended for human food consumption, the use of neurotoxic parasiticidal agents is prohibited since these substances contaminate the food chain, as stated in the European directives on biocides (98/8 EC) and on plant protection (91/414 EEC). It also presents risks to the breeders.

It is also known that parasiticidal compositions based on natural or synthetic essential oils or on pyrethroids or on organophosphorus compounds used as alternatives to organochlorine compounds have an efficacy that decreases rapidly over time. These parasiticidal compositions have an action that may be termed a "shock action". Their efficacy is generally of the order of a few days, and at most of the order of a few weeks. This is due to non-zero vapor pressures of the components that give rise to their volatilization over time and moreover to their degradation by oxidation.

Parasites that have been eliminated at one particular moment may reinfest a livestock unit in the course of livestock production. The toxicity of such compositions, including their toxicity to animals, limits their use on occupied buildings.

Patent WO 01/35744 discloses a parasiticidal composition based on silica. This composition in gel form is free of neurotoxic substances, but is expensive. The composition is not a powder but a granular system which solid particles are surrounded by a liquid phase and behaves as a liquid, as it forms a horizontal surface in a recipient. The aerated gel composition, comprising gelling agent and high amount of water, sticks strongly on treated surfaces. This is an interesting property to fix the silica on treated surfaces but presents the drawback of forming on the treated surface a gelatinous deposit onto which also ambient dust has a tendency to adhere, which reduces its efficacy over time.

Patents WO 2005/025 317 and WO 2006/097 480 disclose various parasiticidal compositions in the form of aqueous suspensions based on an alkali metal bicarbonate, which have the advantage of not being toxic to man and animals. These compositions are applied by brushing or spraying onto the vertical surfaces of the buildings and equipment to be treated. The treatment of a livestock building, for example for rearing laying hens, after sanitary cleaning and mucking out, is usually performed by spraying with suspension. However, the operation requires specific low-pressure or high-pressure industrial spraying machines which represent a certain investment, and the operation requires several hours to apply the aqueous suspension to all the surfaces of the cages and those close to the feeding troughs. The drying of the aqueous suspensions is itself effective within a few minutes to a few hours depending on the applied thickness.

Patent WO 2006/097 504 discloses a parasiticidal composition in powder form based on an alkali metal bicarbonate, which may be applied by dusting onto the horizontal surfaces of buildings occupied by livestock on the ground. Here also, the treatment of ground surfaces requires several hours of work when large surfaces such as those of livestock buildings need to be treated, despite the use of specific equipment. Moreover, the floor is often made of slotted floorings or gratings, through which the animal droppings fall. When these slotted floorings are covered with product in powder form, the animals walking on these slotted floorings remove the product from the floor; this makes regular retreatment of these surfaces necessary.

The invention is directed towards providing an alternative disinfestation process that affords an appreciable saving both in application time and in investment on specific machines, which offers lasting efficacy in the control of parasites that develop on animals and in their environment.

SUMMARY OF THE INVENTION

The invention relates to a process for controlling the development of parasites in the environment of animals equipped an air introduction device with at least one introduction point, according to which a parasiticidal powder composition is introduced into the air introduction device. The invention also relates to the use of the process.

In the present document a powder means a granular media made of solid particles and surrounded by a gaseous phase, which is the common definition of a powder. As for instance, a suspension of solid particles in a liquid is not a powder as the solid particles are surrounded with a liquid phase. One characteristic of a powder is that its surface does not move to a flat horizontal surface in a non agitated container, contrary to a liquid that moves to a flat horizontal surface, whatever the inclination of the container.

The invention also relates to the use of a parasiticidal powder composition in an air introduction device for controlling the development of parasites in an animal environment.

The invention also relates to a device for controlling the development of parasites in the environment of animals, and to a livestock building equipped with such a device.

A first advantage of the present invention is an important gain in time and operator costs to treat large area of a livestock building compared with known prior art.

A second advantage of the present invention is a strong reduction of the quantity of parasiticidal powder composition used per animal compared to known prior art.

A third advantage of the present invention is the possibility to use a safe parasiticidal powder which main components are compatible with food industry requirements.

A fourth advantage of the present invention is the possibility to use a safe parasiticidal powder which main components are also food chemical codex additives and also meet regulations such as 889/2008 EC European directive on organic production and labelling of organic products.

A fifth advantage of the present invention is to decrease risks for the health of breeders and workers as embodiments of present invention reduces concomitantly the quantity of parasiticidal composition to apply in animal environments, reduces sharply the toxicity of the parasiticidal composition, and also enable to workers to be out of the animal environment when proceeding to a treatment.

A sixth advantage of the present invention is to be efficient on large scope of parasites and pests such as acarids, crawling insects, flying insects, and fungi.

A seventh advantage for specific embodiments of the invention, is to leave on droppings of animals in treated environments useful component as alkali bicarbonate, when the animal droppings or manure are further valorized in Biogas production.

DETAILED DESCRIPTION OF THE INVENTION

Buildings in which animals are present, in particular rearing buildings, must ensure an air renewal and adequate indoor temperature for the animals. In particular air introduction enables to maintain an indoor air renewal, a temperature, a humidity level, a level of dust and gas concentrations in adequate levels in the animal environment for their health. Regulations, such as the 1999/74/EC European directive for laying hens, lay down minimum standards for the protection of animals, to keep a balance between welfare and health of the animals and economic, social and environmental considerations. The handling and storage of animal manure or droppings in an animal environment may need also air introduction for sanitary reasons; In particular cases, specific air introduction is used to dry partially droppings and/or manure, particularly when mechanized evacuations devices are used in stables or in rearing buildings.

In the present invention, the device for introducing air into the animal environment is a device suited for transporting the parasiticidal powder composition into the animal environment. This device may be chosen from one of the following devices: aeration grille, air capacity under pressure, forced motorized ventilation, and combinations thereof. Aeration grille, forced motorized ventilation, and combinations thereof are preferred.

In one advantageous embodiment of the invention, the aeration grille is a grille placed on a building wall associated with one or more secondary aeration grilles, arranged such that the outdoor air flow passing through the aeration grille into the animal environment has a sufficient velocity to entrain a parasiticidal composition in pulverulent powder form. The outdoor air may be taken directly outdoor of the animal environment, or taken from another part of a building if adequate to renew the air.

In another advantageous embodiment of the invention, the air introduction device is an airing device comprising at least one appliance that forces the airing of the said environment, and according to which the parasiticidal composition is introduced upstream or downstream the at least one appliance that forces the airing, preferably upstream the at least one appliance that forces the airing. The appliance that forces the airing may be chosen from equipment known to those skilled in the art, such as electrical, pneumatic or mechanical motor-driven fans. In particular, it may be chosen from fans, turbofans and ejectors. Fans are particularly suitable.

The above embodiments are particularly advantageous when the air introduction device is a permanent ventilation device of the animal environment. In the present description, the term "permanent ventilation device" means a ventilation device that is permanently fixed to the animal environment, for instance fixed to a stable or to a rearing building. Examples of permanent ventilation device are: building venting devices or systems, and/or devices aiming at drying partially the animal droppings. The use of a permanent ventilation device in the present invention enables to use part of the existing equipments of such buildings, reducing therefore the cost and the investment to use present invention. The permanent ventilation device may not be used permanently, or may be used at variable air flows, according to the seasons and indoor air conditions to maintain, though it can be turned on when applying the parasiticidal powder composition.

The permanent ventilation device also often includes a heater and/or a cooler to maintain indoor air temperature in adequate levels for the animal. The possibility to heat the air introduced with the permanent ventilation device in the cold season enables to desaturate the introduced air regarding humidity if outdoor air is close to its dew point temperature. Such heating device decreases the risk that the parasiticidal powder composition sticks on the air introduction device, for instance on ventilation forcing equipments and air ducts if humidity condenses on such equipments. Typical air-flows generated by air introduction device ranges:

from 1 to 5 $m^3$/h per kg of animal for a barn or a rearing building venting device, from 0.5 to 2 $m^3$/h per kg of animal for a device aiming at drying partially the animal droppings.

According to one recommended embodiment of the invention, the air introduction device comprises one or more point(s) for introducing air into the animal environment, which is(are) located close to animal droppings. In the present invention, the term "close to the animal droppings" means a distance preferably not more than 10 meters, more preferably not more than 5 meters, or even not more than 2 meters and most preferably not more than 1 meter. In one even more recommended embodiment, the point(s) of introduction of air into the animal environment are placed in immediate proximity to the transporters or belts for removing the animal droppings. In another recommended embodiment the air introduction device is a device aiming at drying partially the animal droppings. In the case of livestock in a cage, such as that of laying hens, it is particularly advantageous for the air introduction device to be the device for drying the droppings located on the belts, which are themselves under the lower grilled part of the cages.

In any of the above embodiments, the parasiticidal powder composition consists of particles, in which said particles preferably have a particle size distribution such that at least 75% in weight of the particles have a diameter of less than 100 μm and more preferably such that at least 90% in weight of the particles have a diameter of less than 70 μm. The diameters are measured according to standard ASTM C-690-1992. Such a form of the parasiticidal composition enables efficient diffusion of the parasiticidal composition by the air introduction device into the animal environment. The parasiticidal composition is then dusted as a fine layer in the animal environment. The parasites moving in contact with the parasiticidal composition cannot then survive.

In one advantageous embodiment of the invention when the air introduction device is an airing device comprising at least one appliance that forces the airing of the said environment, the parasiticidal powder composition is introduced gradually into the airing device by means of a mechanized or a manual device. The mechanized device may be chosen from bottomless hoppers, screw-feed solid metering devices, hopper devices equipped with a rotary trefoil, hopper devices equipped with slide-gate valves, conical hopper devices equipped with knife-edge mixer-feeders, and combinations thereof. The manual device may be chosen from bottomless hoppers, funnels, buckets, troughs, metering cups, metering shovels, and combinations thereof. The powder is then introduced gradually into or via the said device over a time of at least one second, or at least 2 seconds, or of at least 5 seconds, or of at least 10 seconds. In one particular mode of this advantageous embodiment, the powder is introduced into the said device continuously, or preferably over a time of not more than 10 minutes, more preferably not more than 5 minutes, or more preferably not more than 1 minute.

In any one of the above embodiments, the parasiticidal composition advantageously comprises an alkali metal bicarbonate and/or silica.

In the process according to the invention, the alkali metal bicarbonate may, for example, be bicarbonate in the strict sense such as potassium bicarbonate or sodium bicarbonate. However, in this document, it also covers compound salts such as alkali metal sesquicarbonates (for example trona) which comprise bicarbonate. Sodium or potassium bicarbonates or trona are especially suitable for use. Bicarbonates in the strict sense are recommended. Potassium bicarbonate or sodium bicarbonate, more particularly sodium bicarbonate, are preferred. In certain cases, however, potassium bicarbonate is more preferred.

In the particular embodiment of the present invention, in which the parasiticidal powder comprises an alkali metal bicarbonate and/or silica, the powder advantageously comprises at least 60%, preferably at least 70% and even more preferentially at least 80% by weight of bicarbonate. Bicarbonate has its own parasiticidal action.

In the particular embodiment of the present invention, in which the parasiticidal composition in powder form comprises an alkali metal bicarbonate and/or silica, the parasiticidal composition comprises at least 1% and preferably at least 5%, more preferably at least 10% by weight of silica. The amount of water, as humidity or as water molecules inside in the parasiticidal composition, has an impact on the flowability of the powder. Moreover a high amount of water gives rise to high adhering properties of the powder to the surfaces of the air introduction device. This may leads to plugging of air ducts and unbalance rotation of rotating devices such as fan. In present invention it is recommended that the parasiticidal powder composition comprises less than 30%, advantageously less than 25%, more advantageously less than 20%, preferably less than 10%, more preferably less than 5%, even more preferably less than 3%, most preferred less than 2% in weight of water.

When silica is combined with alkali metal bicarbonate, it is recommended that the parasiticidal powder composition comprises at most 20% and preferably at most 15% thereof.

In present invention when the parasiticidal comprises silica, the silica preferably comprises less than 4 w. % of crystalline silica, more preferably less than 0.1 w. % of crystalline silica. Mineral compounds comprising silica ($SiO_2$) such as diatomaceous earth, preferably non calcined diatomaceous earth, or clays such as bentonite, may be used. Non calcined diatomaceous earth comprises generally between 0.1 and 4 w. % of crystalline silica. Though it is recommended that the silica be in amorphous form (and not crystalline) for its tolerance by the human or animal body. More preferably in present invention the parasiticidal powder composition is free of diatomaceous earth. And even more preferably the parasiticidal powder composition is free of crystalline silica.

It is preferable for the silica to be in the form of very fine particles, with a high specific surface area, for example greater than 200 $m^2/g$ and preferably 400 $m^2/g$, measured according to standard ISO 5794-1, annex D. In one advantageous embodiment of the invention, the silica is in the form of particles with a mean diameter of less than 10 μm. The mean diameter is measured according to standard ASTM C-690-1992.

Amorphous silica is a silica that is nutritionally neutral, and is a compound registered on the list of mineral products of the Codex Alimentarius of the FAO (Food and Agriculture Organization) and of the WHO (World Health Organization).

It has been observed that when the parasiticidal composition is in powder form and simultaneously comprises an alkali metal bicarbonate and a silica, the powder has excellent fluidity. It generates virtually no bonding or adhesion of powder to the walls of the introduction device. Specifically, synergism between the two components of the powder is created: the silica affords very good flowability to the powder, and the alkali metal bicarbonate affords a light abrasive effect of the powder, bringing about a self-cleaning effect on any powder deposits in the air introduction devices.

The parasiticidal powder may comprise essential oils for their known parasiticidal effects, specifically neurotoxic effects for insects. Though high amount of essential oils are detrimental to powder fluidity and glues the powder to surfaces such as air ducts. Moreover essential oils are irritating for eyes or respiratory organs of human and animals. Therefore the parasiticidal powder composition in present invention comprises advantageously less than 5%, preferably less than 2%, more preferably less than 0.5% in weight of essential oils; even more preferably the parasiticidal powder composition is free of essential oils.

In any one of the above embodiments, the parasiticidal powder composition is advantageously free of neurotoxic substances.

In another particularly advantageous embodiment, when the parasiticidal composition comprises an alkali metal bicarbonate and/or silica, the parasiticidal composition is free of parasiticidal active ingredients other than silica and alkali bicarbonate. Specifically, alkali metal bicarbonates and silica are substances that are not harmful to man or animals. In the case of sodium and potassium bicarbonates, they are permitted by various bodies (such as the Food and Drug Administration in the United States and the EEC, the Food and Agriculture Organization, and the WHO) in human and animal nutrition. In this particularly advantageous embodiment, the alkali metal bicarbonate is preferably sodium bicarbonate.

The process according to the invention is effective against parasites in numerous animal environments, including certain human environments. The term "environment" means all the surfaces on which the parasites may alight, move around or develop. This environment includes, for example, the floors of dwellings, caves, lofts or livestock buildings, these buildings comprising cages, laying nests, boxes, litters and beds.

The parasites that develop on livestock are extremely varied: fleas, lice, bugs and ticks are especially encountered. The process according to the invention is used in the animal environment to control the development of insects such as fleas, lice and beetles, and the development of mites such as ticks and sarcoptics. According to one advantageous variant of the process according to the invention, the parasites are mites. The process is especially effective against *Dermanyssus gallinae*. These parasites have a tendency to develop abundantly in the environment of laying hens. They are intermittent parasites. They do not always remain on contact with animals. They are killed upon contact with the animal's treated environment.

Livestock buildings also suffer from the presence of numerous molds and fungi of various types, for instance *Aspergillus*, especially *fumigatus*. The use of bicarbonate in the parasiticidal composition according to the invention also makes it possible to combat their development. Consequently, the invention also relates to the use of the process according to the invention for its combined parasiticidal and antifungal effects.

The process according to the invention may be used for controlling the development of parasites in the environment of any type of livestock. Examples that may be mentioned include cattle, sheep, goats, rabbits, poultry, birds and pigs. Disinfestation of their environment improves the growth and development of these animals, and increases the productivity of the livestock. Consequently, according to one recommended embodiment of the process according to the invention, the animals are livestock and the environment is in particular the building in which the animals are reared.

According to one recommended embodiment of the process according to the invention, the livestock is poultry, such as laying hens, or table chickens and turkeys. It has been observed that the treatment according to the invention of their environment allows good egg production by laying hens and good growth of the hens, by virtue of the elimination of the parasites.

The process is particularly advantageous for the rearing of laying hens. Specifically, the process according to the invention allows effective control of the development of red mites, such as *Dermanyssus gallinae*, which are vectors for the transmission of certain types of salmonellosis that may attack the eggs and that are, moreover, liable to degrade the visual quality of the eggs by generating marks on the surface of the eggs.

When the parasiticidal composition comprises an alkali metal bicarbonate and/or silica, the parasiticidal composition is introduced into the air introduction device in an amount per application of at least 5, preferably of at least 10, more preferably of at least 20 and most preferably of at least 40 mg per kg of animal. It is not necessary to introduce the parasiticidal composition into the air introduction device in an excessive amount, otherwise the animal environment will be made dusty and slippery. It is recommended to introduce the parasiticidal composition into the air introduction device in an amount per application of at most 2000, preferably at most 500, more preferably at most 125 and most preferably at most 80 mg per kg of animal.

According to the process of the invention, it is moreover recommended for the frequency of application of the parasiticidal composition to be at least every two months, preferably at least monthly, more preferably at least fortnightly and most preferably at least weekly.

Thus, an application in accordance with the process of the invention requires several tens of operator seconds to several operator minutes, which may be repeated regularly, instead of three to four operator hours for a traditional direct treatment of the surfaces by dusting or spraying under pressure of a parasiticidal agent or insecticide.

Moreover, the amount of parasiticidal composition in powder form remains limited. Thus, at a rate of 75 mg of powder per hen and per weekly application, the amount of parasiticidal composition is limited to 4 g of powder per hen and per year. At a rate of 100 mg of powder per hen and per weekly application, the amount of parasiticidal composition is 5 g of powder per hen and per year. For animals reared in slow-growing conditions avoiding intensive rearing methods, and reared for less than one year (for instance 81 days chicken, 49 days Pekin ducks, 140 days male turkey, 150 days capons, 6 months pigs or small ruminants) the amount of parasiticidal powder used therefore reported to an animal and normalized according its weight is even less compared to prior art. For instance in prior art when a parasiticidal composition is to be used at 7 g per hen in a first treatment, then renewed after one week at 7 g, and then renewed every 3 or 4 months at 3 g per hen, the total annual quantity in this case is about 25 g+/−2 g per hen and per year. In comparison, 4 or 5 g per hen and per year are typically used in the present invention.

Such small amounts of parasiticidal powder per treatment, using preferably 5 to 80 mg of parasiticidal powder per kg of animal, enable also to decrease temporary pick dust concentration when the parasiticidal powder is applied in the indoor air of the animal environment to levels, and also the amount of residual dust indoor. It is observed that when treated with quantities of at most 2000, or at most 500, or at most 125, or at most 80 mg per kg of animal, the animal environment is particularly less dusted compared to prior art using for instance 7 g per hen of parasiticidal powder treatments; though with excellent results in parasite control.

In a particularly advantageous embodiment of the present invention, the parasiticidal powder composition comprises at least 1% silica, and at least 60% alkali bicarbonate, preferably at least 60% sodium bicarbonate, and less than 30% of water, and the parasiticidal powder composition consists of particles, in which said particles have a particle size distribution such that at least 75% in weight of the particles have a diameter of less than 100 μm, wherein the air introduction device comprises at least one point for introducing air into the animal environment which is located close to animal droppings, and wherein the parasiticidal powder composition is introduced into the air introduction device in an amount per application of at least 5 mg and at most 2000 mg per kg of animal, and the frequency of application of the parasiticidal composition is at least every two months.

Consequently, the present invention also relates to the use of the present process for controlling the development of parasites in an animal environment in any one of the embodiments described above.

Consequently, the invention also relates to the use of a parasiticidal composition in an air introduction device for controlling the development of parasites in an animal environment in any one of the embodiments described above.

The invention also relates to a device for facilitating the use of the process according to the invention. According to one of the embodiments, the device for controlling the development of parasites in an animal environment comprises:

- at least one air duct for introducing air, preferably outdoor air, at at least one point of introduction in the animal environment,
- at least one appliance for forcing the circulation of air in at least one aeration conduit, and preferably able to produce in all or part of the at least one aeration conduit an air circulation velocity of at least 0.5, preferably of at least 1, more preferably of at least 2 and most preferably of at least 5 m/s,
- at least one device able to introduce a parasiticidal powder into the said aeration conduit upstream or downstream of at least one appliance for forcing air circulation, preferably upstream of the at least one appliance for forcing air circulation.

In the above device, the appliance for the circulation of air flow in the at least one air duct is able to force the circulation of air at a flow rate of advantageously at least 1 m$^3$/h per kg of animal.

The aeration conduit may be of any shape with cylindrical or rectangular cross sections. It is made of plastics or metals. Plastics are preferred.

The plastics that may be used advantageously consist of polyolefins (such as charged polyethylene or polypropylene), PVC or PVDF. PVC is preferred. When the aeration conduits are made of plastic, this plastic is advantageously filled with mineral fillers in order to give it sufficient impact strength for use in industrial or agricultural environments. The surface state of the aeration conduits is preferably chosen from "smooth" interior finishes. Conduit interior surface states having few or no irregularities greater than 10 μm, advantageously 5 μm and more advantageously 2 μm in size are preferred. The "smooth" aspect makes it possible to limit any attachment of the parasiticidal composition when it is in powder form.

The plastics that may be used for the aeration conduit are advantageously steel and more advantageously food-grade stainless steel. Zinc-plated steel and aluminum are less favorable since they are corrodible.

In one advantageous embodiment of the device according to the invention, the aeration conduit is equipped at the end of straight section(s) with opening device(s) allowing the passage of tools for cleaning and brushing the interior of the straight section(s) of the conduit.

The conduit elbows are advantageously chosen from those with a large radius of curvature; if D is the diameter of the conduit or one of its characteristic internal dimensions, the radii of curvature are advantageously at least 3D and preferably at least 5D.

The connections between straight or bent sections of the conduit are advantageously assembled by joining together and without a joint penetrating into the conduit.

The equipment that forces air circulation in the at least one aeration conduit is chosen from fans, turbofans and ejectors. The equipment is advantageously chosen from fans.

The device for introducing the parasiticidal powder into the said aeration conduit is selected from bottomless hopper devices, screw-feed solid metering devices equipped with powder storage capacity, hopper devices equipped with a rotary trefoil, hopper devices equipped with slide-gate valves, conical hopper devices equipped with knife-edge mixer-feeders, and combinations thereof.

When the equipment for forcing air circulation is selected from turbofans or ejectors, the device for introducing the parasiticidal powder is advantageously placed downstream of the equipment.

When the equipment for forcing air circulation is selected from fans, the device for introducing the parasiticidal powder is advantageously placed upstream of the equipment.

In the present specification, the term "downstream" means: after the equipment for forcing air circulation relative to the main direction of circulation of air in the device for controlling the development of parasites in an animal environment. In the present specification, the term "upstream" means: before the equipment for forcing air circulation relative to the main direction of circulation of air in the device for controlling the development of parasites in an animal environment.

The point of introduction of air at at least one introduction point into the animal environment of the present invention is advantageously located close to the animal droppings. The air introduction point may be equipped with deflectors. Advantageously, the air introduction point(s) consist of one or more slits on the aeration conduit.

In the case of devices for laying hens and table chickens and turkeys, the point of introduction of air at at least one introduction point in the animal environment of the present invention is advantageously located under the lower grilled part of the cages. In this case, preferably, the air introduction point is located on the droppings evacuation belt, under the lower grilled part of the cages.

The invention also relates to a livestock building equipped with a device for controlling the development of parasites according to the present invention.

EXAMPLES

The following example serves to illustrate the invention. It is not limiting and may be transposed to other animals and other types of rearing environment.

Example 1

In Accordance with the Invention

A rearing building that may contain 40 000 battery laying hens is equipped with an air introduction device for drying droppings. Mechanized belts installed under the animal cages receive the droppings. Each battery has an aeration duct. The duct has a slit for introducing air at a height about 15 cm above the belts. Each day, the droppings belts are activated in order to advance and evacuate the droppings.

In the present example, a parasiticidal powder Bi-Protec® from the company Solvay Carbonate France was used. This powder is in accordance with that described in patent EP 1 860 948 and used in Examples 1 to 5 of the said patent.

Once a week, a thorough treatment based on Bi-Protec® is performed according to the process of the present invention. To do this, the belts are activated to evacuate the droppings from the belts, and the cross-ventilation in the livestock building for controlling the temperature of the building is reduced by switching off every other cross-fan and by halving the velocity of the cross-fans that remain functional, thus preventing the parasiticidal powder from being evacuated out of the building too quickly, and then, over a period of 2 minutes, 4.5 kg of Bi-Protec® powder are introduced into the suction of the fan of the air introduction device for drying the droppings. This amount of Bi-Protec® corresponds to 77 mg of Bi-Protec® per laying hen and per week, i.e. about 40 mg per kg of animal and per week. It is observed after treatment that the Bi-Protec® powder is uniformly distributed in the livestock building as a fine layer on the structures of the building, the equipment and the surfaces of the cages. Approximately one hour after the treatment with Bi-Protec®, the cross ventilation of the building is switched back on.

The corresponding amount of Bi-Protec® used over a year at a rate of once a week according to the procedure described above thus corresponds to 4 g per laying hen.

After a few weeks of use of the process, good control of the development of *Dermanyssus gallinae* (red mites) is observed in the livestock building that was initially infested with red mites: most of the red mites observed, adults or young, are dead.

After six months of use of the process in the livestock building, this building remains very clean, few or no live *Dermanyssus gallinae* (red mites) are observed, and similarly few or no other mite or insect parasites are observed on the structures of the building, the cages and the laying boxes. The hens are particularly calm, especially when compared with the usual livestock buildings or with buildings in which the red mites are not treated. The air introduction circuits used for dispersing the parasiticidal powder are clean.

Example 2

Comparison on Sprayability and Dispersibility of Different Parasiticidal Compositions In this test, parasiticidal compositions detailed in table 1, are sprayed with dry air (dew point at 0° C.) at 2 bar pressure to form a jet with an air velocity of about 14 m/s and a parasiticidal composition weight ratio to air of about 60 w. % on standard glass microscope lamella fixed horizontally at 60 cm of the spray jet outlet. The spray jet axis is inclined at an angle of 45° relatively to the lamella horizontal plane.

After 30 seconds the powder sprays is stopped and the glass lamella is removed to be examined with an optical microscope at an enlargement ratio of ×5. Observations on the experiment and microscope observations are detailed in Table 2.

For Test E to G, the cogrinding operating conditions of the parasiticidal powder preparation are the ones described in Example 1 (mode 2) of FR1161937 (Solvay). For this, a 3-liter useful capacity Lödige plough mixer was used to mix the powders in the desired proportions. The mixture is then grinded on a UPZ100 Hosokawa-Alpine grinder using a stainless steel pin-mill rotor/stator at 17 600 revolutions/min, the mixture being fed in the grinder at 1.5 kg/h.

Should the disclosure of any of the patents, patent applications, and publications that are incorporated herein by reference conflict with the present specification to the extent that it might render a term unclear, the present specification shall take precedence.

TABLE 1

Parasiticidal composition of Example 2.

| Test | Parasiticidal composition and content in weight percent (w %) | Silica w. % | Alkaline Bicarbonate w. % | Water w. % |
| --- | --- | --- | --- | --- |
| A | Silica Sipernat 50S/Evonik (powder) | >98 | 0 | <2 |
| B | Silica Tixosyl 38AB/Rhodia-Solvay (powder) | >98 | 0 | <2 |
| C1 | Composition according to example 1 of WO01/35744A1 Hydrophobe Silica CAB-O-SIL TS270 from Cabot with 0.5% xantham gum (liquid gel). | 3 | 0 | 96.5 |
| C2 | Composition according to example 1 of WO01/35744A1 with decreased ratio of water to Hydrophobe Silica CAB-O-SIL TS270 from Cabot with 0.5% xantham gum (humid powder). | 70 | 0 | 29.5 |
| D | Sodium bicarbonate Bicar® 0/4 Solvay 100% < 40 µm and Sipernat 50 S mixed in a Lödige plough mixer 5 minutes (powder). | 15 | 85 | <0.3 |
| E | Sodium bicarbonate Bicar® Z/ Solvay and Tixosyl 38AB co-ground according Example 1 (mode 2) of FR1161937 (Solvay) (powder). | 15 | 85 | <0.5 |
| F | Sodium bicarbonate Bicar® Z and Perlite 55 co-ground (same operating conditions as powder of Test E). (powder) | 15 | 85 | <0.5 |
| G | Potassium bicarbonate of mean weight diameter size distribution of 40 µm and Perlite 55 co-ground (same preparation conditions as powder of Test E). (powder) | 18 | 82 | <0.5 |

TABLE 2

Test Comment and Microscope observation of glass lamella of Example 2.

| Test | Test Comment and Microscope observation of glass lamella |
| --- | --- |
| A | Fine layer of powder particles on the glass surface. Frequent agglomerates (soft flakes) of more than 150 µm, large size span of agglomerates. The powder does not adhere to the glass, a simple whisper blow is sufficient to remove most of the powder. |
| B | Idem A |
| C1 | Coarse layer of gel composition adhering strongly to the glass. Difficulty to spray. A whisper blow is not sufficient to remove most of the gel. Noticeable adherence of the composition on spray jet outlet. |
| C2 | Layer of powder adhering slightly to the glass. |
| D | Fine layer of powder particles on the glass surface. Some agglomerates (soft flakes) of more than 150 µm but less than tests A and B. The powder does not adhere to the glass, a simple whisper blow is sufficient to remove most of the powder. |
| E | Idem D. Powder well dispersed on the lamella. The powder does not adhere to the glass, a simple whisper blow is sufficient to remove most of the powder. |
| F | Idem E |
| G | Idem E |

The invention claimed is:

1. A process for controlling the development of parasites in an animal environment equipped with an air introduction device, comprising introducing a parasiticidal powder composition into said air introduction device in an amount per application in the animal environment of at least 5 mg per kg of animal.

2. The process according to claim 1, wherein said air introduction device is an airing device comprising at least one appliance that forces the airing of said animal environment, and wherein said parasiticidal composition is introduced upstream or downstream of said at least one appliance that forces the airing.

3. The process according to claim 1, wherein said air introduction device is a permanent ventilation device of said animal environment.

4. The process according to claim 1, wherein said air introduction device comprises at least one point for introducing air into said animal environment, and wherein said at least one point for introducing air is located close to animal droppings.

5. The process according to claim 4, wherein said air introduction device is a device aiming at drying partially said animal droppings.

6. The process according to claim 1, wherein said parasiticidal powder composition consists of particles, and wherein said particles have a particle size distribution such that at least 75% in weight of the particles have a diameter of less than 100 μm.

7. The process according to claim 1, wherein said parasiticidal powder composition comprises at least 1% by weight of silica.

8. The process according to claim 1, wherein said parasiticidal powder composition comprises less than 30% by weight of water.

9. The process according to claim 1, wherein said parasiticidal powder composition comprises an alkali metal bicarbonate.

10. The process according to claim 1, wherein said parasiticidal powder composition comprises less than 5% by weight of essential oils.

11. The process according to claim 10, wherein said parasiticidal powder composition is free of essential oils.

12. The process according to claim 1, wherein said parasiticidal powder composition is free of neurotoxic substances.

13. The process according to claim 1, wherein said parasiticidal powder composition is free of other parasiticidal active ingredients other than silica and alkali bicarbonate.

14. The process according to claim 1, wherein said animal environment is for a livestock animal, and wherein said animal environment is a building in which a livestock animal is reared.

15. The process according to claim 1, wherein said parasiticidal powder composition is introduced into said air introduction device in an amount per application of at least 10 mg per kg of animal.

16. The process according to claim 1, wherein said parasiticidal powder composition is introduced into the air introduction device in an amount per application of at most 2000 mg per kg of animal.

17. The process according to claim 1, wherein said parasiticidal composition is applied with a frequency of at least every two months.

18. The process according to claim 1, wherein said parasiticidal powder composition comprises at least 1% by weight silica, at least 60% by weight of alkali bicarbonate, and less than 30% by weight of water; wherein said parasiticidal powder composition consists of particles wherein said particles have a particle size distribution such that at least 75% by weight of the particles have a diameter of less than 100 μm; wherein said air introduction device comprises at least one point for introducing air into said animal environment, said at least one introduction point being located close to animal droppings; wherein said parasiticidal powder composition is introduced into said air introduction device in an amount per application of at least 5 mg and at most 2000 mg per kg of animal, and wherein said parasiticidal composition is applied with a frequency of at least every two months.

19. The process according to claim 1, wherein said parasiticidal powder composition comprises sodium bicarbonate.

20. A device suitable for carrying out the process for controlling the development of parasites in an animal environment according to claim 1, comprising:
- at least one air duct for introducing outdoor air at at least one point of introduction in said animal environment,
- at least one appliance for forcing the circulation of air in said at least one air duct to produce in all or part of the at least one air duct an air circulation velocity of at least 0.5 m/s,
- at least one device able to introduce an amount of at least 5 and at most 2000 mg/kg of animal of a parasiticidal powder into said air duct upstream or downstream of said at least one appliance for forcing air circulation.

21. The device according to claim 20, wherein said appliance for the circulation of air flow in said at least one air duct is able to force the circulation of air at a flow rate of at least 1 m³/h per kg of animal.

* * * * *